United States Patent
Contreras et al.

(10) Patent No.: US 10,279,147 B2
(45) Date of Patent: May 7, 2019

(54) ARTICULATION DEVICE HAVING INCREASED VISIBILITY

(71) Applicant: Centerline Medical, LLC, Redwood City, CA (US)

(72) Inventors: Marcos T. Contreras, Sunnyvale, CA (US); Ronald G. Williams, Menlo Park, CA (US)

(73) Assignee: Centerline Medical, LLC, Redwood City, CA (US)

( * ) Notice: Subject to any disclaimer, the term of this patent is extended or adjusted under 35 U.S.C. 154(b) by 0 days.

(21) Appl. No.: 15/612,575

(22) Filed: Jun. 2, 2017

(65) Prior Publication Data

US 2018/0344980 A1    Dec. 6, 2018

(51) Int. Cl.
| | |
|---|---|
| *A61M 25/01* | (2006.01) |
| *A61B 1/005* | (2006.01) |
| *A61M 25/00* | (2006.01) |
| *A61B 1/00* | (2006.01) |

(52) U.S. Cl.
CPC ....... *A61M 25/0147* (2013.01); *A61B 1/0057* (2013.01); *A61M 25/0043* (2013.01); *A61B 1/0008* (2013.01); *A61M 25/0009* (2013.01); *A61M 2025/015* (2013.01)

(58) Field of Classification Search
CPC .......... A61M 25/0147; A61M 25/0043; A61M 25/0009; A61M 2025/015; A61B 1/0057; A61B 1/0008
See application file for complete search history.

(56) References Cited

U.S. PATENT DOCUMENTS

| | | |
|---|---|---|
| 6,221,059 B1 | 4/2001 | Chiang et al. |
| 6,261,219 B1 | 7/2001 | Meloul et al. |
| 6,544,215 B1 | 4/2003 | Bencini et al. |
| 8,048,026 B2 | 11/2011 | Fischer et al. |
| 8,273,054 B2 | 9/2012 | St. Germain et al. |
| 8,540,697 B2 | 9/2013 | Honebrink et al. |
| 8,641,604 B2 | 2/2014 | Golden et al. |
| 8,758,420 B2 | 6/2014 | Dorn et al. |
| 9,044,248 B2 | 6/2015 | Benscoter et al. |
| 2013/0281925 A1* | 10/2013 | Benscoter ............ A61B 1/0125 604/95.04 |
| 2016/0114133 A1 | 4/2016 | Thorstenson et al. |

* cited by examiner

*Primary Examiner* — Amber R Stiles
(74) *Attorney, Agent, or Firm* — Kilpatrick Townsend and Stockton LLP

(57) ABSTRACT

Articulation devices, such as comprising pull rings, are provided having improved or increased visibility under conventional visualization techniques, such as fluoroscopy. Such improved visibility is achieved by the presence of at least one insert comprised of a material that is more visible or detectable under imaging techniques than the pull ring. The at least one insert is positionable within a cut-out in the articulation device and fixed into place by a suitable method such as adhesive, soldering, swaging, welding, laser welding, etc. The insert resides within the dimensions of the walls of the pull ring so as to not increase the outer diameter or decrease the inner diameter of the pull ring. This maintains the profile of the overall articulation device. Thus, the one or more inserts can improve the radiopacity of the pull ring, allowing the pull ring to be more visible and more easily identifiable under fluoroscopy than a conventional pull ring without negatively altering other features such as tensile strength or overall dimensions of the pull ring.

15 Claims, 5 Drawing Sheets

ARTICULATION DEVICE HAVING INCREASED VISIBILITY

BACKGROUND OF THE INVENTION

A variety of devices have an articulating distal end which is controlled by a mechanism disposed along its proximal end. This allows remote articulation of the distal end and is particularly useful for situations wherein the distal end is not accessible. In medical devices, a variety of catheters and surgical instruments have elongate distal ends which are introducible into the body for various treatment procedures. Typically, the proximal end includes a handle which remains outside of the body and includes mechanisms for controlling and articulating the distal end which is remote and inaccessible.

FIG. 1 illustrates an example catheter 10 comprising an elongate shaft 12 and handle 16. Here, the elongate shaft 12 is articulatable along its distal end 14 for steering and maneuvering remotely. In this example, such articulation is achieved with the use of a pull ring 20 positioned around the elongate shaft 12 near the distal end 14 which is connected to a pull wire 22 which extends along the shaft 12 toward a proximal end 18. In this example, the pull wire 22 is connected to a rotating cuff 24 along the handle 16, wherein rotation of the cuff 24 applies pulling force to the pull wire 22 which causes bending of the distal end 14 as indicated by the dashed line image. In this example, rotation of the cuff 24 in the opposite direction releases the pulling force and allows the distal end 14 to recoil to its original position. It may be appreciated that a pull ring 20 may have multiple pull wires 22 for articulation in various directions, and/or a catheter 10 may have multiple pull rings 20 for various types of articulation.

Typically, pull rings 20 and their attached pull wires 22 are comprised of stainless steel due to the large forces applied for articulation. In some instances, a pull ring 20 with a 0.010 inch pull wire 22 having an ultimate tensile strength of 27 lbf will have a design requirement of 15-20 lbf. Or, a pull ring 20 with a 0.015 inch pull wire 22 having an ultimate tensile strength of 62 lbf may have a design requirement of 40-50 lbf.

Typically, the pull ring 20 is cut from full-hard stainless steel tubing and includes a slot 30 which is laser cut into the wall of the tubing for insertion of the pull wire 22, as illustrated in FIG. 2. In this example, the pull ring 20 is cut from tubing having an outer diameter of 0.230 inches and an inner diameter of 0.200 inches, thus having a wall thickness of 0.015 inches. The pull wire 22 is then welded to the wall of the tubing to fix the pull wire 22 in place. Such welding is usually low energy so that the pull wire 22 is not significantly damaged. In this example, the pull wire 22 has a diameter of 0.015 inches. In most instances, the pull ring 20 is has a length that is as short as practical to minimize stiffness of the catheter shaft 12 when placed therearound, allowing the catheter to easily track over a guidewire or pass through an introducer. In this example, the pull ring 20 has a length of 0.150 inches. In addition, the slot 30 is typically cut as long as practical to maximize the weld length (allowing the use of low energy) so that the pull wire 22 does not fail in shear. This combination of design features, particularly low energy welds over a long distance, maximizes the ultimate tensile strength of the weld so as to approach the ultimate tensile strength of the wire.

Since the distal end 14 of the catheter 10 is within the patient during use, the user is unable to visualize the articulation of the distal end 14. In most situations, such visualization is achieved by the use of fluoroscopy. In some instances, one or more marker bands are positioned along the catheter shaft 12 wherein the marker bands are comprised of a radiopaque material, such as gold or platinum, which is visible under fluoroscopy. However, such bands add additional cost, labor and dimension to the catheter 10. In some instances, pull rings 20 may be used to assist in visualization of the articulating end, however thin bands of stainless steel are difficult to easily identify under fluoroscopy, particularly amid other devices used in conjunction with the articulating catheter and other hardware that may have been previously installed in the patient.

Consequently, pull rings 20 have been modified to increase their visibility under fluoroscopy. For example, stainless steel pull rings 20 have been plated in gold to increase their visibility. Such plating is typically 0.002 or 0.003 inches thick. This significantly increases the wall thickness of the pull ring 20, such as adding dimension to the inner diameter and outer diameter of the pull ring 20. Thus, the catheter 10 will have an overall larger French size and a smaller lumen through which to pass another device, both of which are contrary to optimization of the catheter 10.

In other instances, platinum marker bands have been positioned adjacent to or on top of stainless steel pull rings 20. Placing the marker band adjacent to the pull ring 20 creates a long region of stiffness along the catheter shaft 12, reducing the flexibility of the shaft 12. Placing the marker band on top of the pull ring 20 increases the diameter of the pull ring 20, which as mentioned increases the overall French size of the device which is disadvantageous.

In yet other instances, platinum marker bands have been attempted to be used as pull rings 20, however platinum is relatively soft even with the addition of elements such as tungsten or iridium. Stainless steel pull wires 22 welded to platinum marker bands will not produce the desired ultimate tensile strength for most design applications where pull rings 20 are used for articulation, leading to breakage of the bond and/or damage to the marker band, pull wire, or catheter.

Therefore, improved methods and devices are desired for visualization of remotely articulating portions of devices or instruments without compromising design features such as profile, inner diameter, outer diameter, flexibility or strength. At least some of these objectives are met by the present invention.

SUMMARY OF THE INVENTION

The present invention generally relates to articulation devices, such as comprising pull rings, having improved or increased visibility under conventional visualization techniques, such as fluoroscopy. Such improved visibility is achieved by the presence of at least one insert comprised of a material that is more visible or detectable under imaging techniques than the pull ring. The at least one insert is positionable within a cut-out in the articulation device and fixed into place by a suitable method such as adhesive, soldering, swaging, welding, laser welding, etc. The insert resides within the dimensions of the walls of the pull ring so as to not increase the outer diameter or decrease the inner diameter of the pull ring. This maintains the profile of the overall articulation device. Thus, the one or more inserts can improve the radiopacity of the pull ring, allowing the pull ring to be more visible and more easily identifiable under fluoroscopy than a conventional pull ring without negatively altering other features such as tensile strength or overall dimensions of the pull ring.

In a first aspect of the invention, an articulation device is provided comprising a tubular pull ring having a first end, a second end and a circumferential wall, wherein the wall includes at least one cut-out; at least one radiopaque insert fixedly inserted into the at least one cut-out so that the insert is disposed within the wall without increasing thickness of the wall; and a pull wire fixedly attached to the pull ring, wherein the tubular pull ring is mountable on a distal end of a shaft so that application of force to the pull wire articulates the distal end of the shaft.

In some embodiments, the radiopaque insert comprises a wire. In other embodiments, the radiopaque insert comprises a ribbon or sheet. In yet other embodiments, the radiopaque insert comprises a polymer or ceramic embedded with radiopaque material.

In some embodiments, the radiopaque insert has a higher radiopacity than the pull ring. For example, in some embodiments, the radiopaque insert is comprised of platinum or gold. This may be particularly the case when the pull ring is comprised of stainless steel.

In some embodiments, the cut-out has a rectangular, oval, round, circular, square or spiral shape. In some embodiments, the cut-out has a shape of a letter, word, number, symbol or logo.

In some embodiments, the radiopaque insert is fixedly inserted by adhesive, soldering, swaging, welding, or laser welding the radiopaque insert to the pull ring. In some embodiments, the at least one cut-out is disposed along the wall of the pull ring in an arrangement which provides an indication of rotational orientation of the pull ring around its longitudinal axis when visualized from one side.

In some embodiments, the articulation device further comprises at least one additional pull wire fixedly attached to the pull ring, wherein the at least one cut-out is disposed between fixation points of the pull wire and the at least one additional pull wire to the pull ring.

In a second aspect of the present invention, an articulation device is provided comprising a tubular pull ring having a first end, a second end and a circumferential wall, at least one radiopaque wire or ribbon fixedly attached to an end surface of the first end or second end of the pull ring without increasing thickness of the wall; and a pull wire fixedly attached to the pull ring, wherein the tubular pull ring is mountable on a distal end of a shaft so that application of force to the pull wire articulates the distal end of the shaft.

In some embodiments, the at least one radiopaque wire or ribbon has the shape of a ring. In other embodiments, the at least one radiopaque wire or ribbon has the shape of a coil.

A method of fabricating an articulation device comprising removing a portion of a wall of a tubular pull ring to create a cut-out; inserting a radiopaque insert into the cut-out so as to not increase thickness of the wall, wherein the radiopaque insert has a higher radiopacity than the pull ring; and fixing the radiopaque insert to the pull ring.

In some embodiments, the radiopaque insert comprises a wire, ribbon or sheet. In some embodiments, inserting the radiopaque insert comprises filling the cut-out with a polymer or ceramic embedded with radiopaque material. In some embodiments, the cut-out has a shape of a rectangle, oval, circle, square, spiral, letter, word, number, symbol or logo.

In some embodiments, fixing the radiopaque insert comprises adhering, soldering, swaging, welding, or laser welding the radiopaque insert to the pull ring.

In some embodiments, removing the portion of the wall of the tubular pull ring to create the cut-out comprises removing the portion of the wall to create the cut-out in an arrangement which provides an indication of rotational orientation of the pull ring around its longitudinal axis when visualized from one side.

In some embodiments, removing the portion of the wall of the tubular pull ring to create the cut-out comprises removing a plurality of portions of the wall to create a plurality of cut-outs arranged so as to provide an indication of rotational orientation of the pull ring around its longitudinal axis when visualized from one side.

In some embodiments, the method further comprises fixedly attaching a pull wire to the pull ring.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device and method will now be described with reference to the drawings. Nothing in this detailed description is intended to imply that any particular component, feature, or step is essential to the invention.

Figure 1:
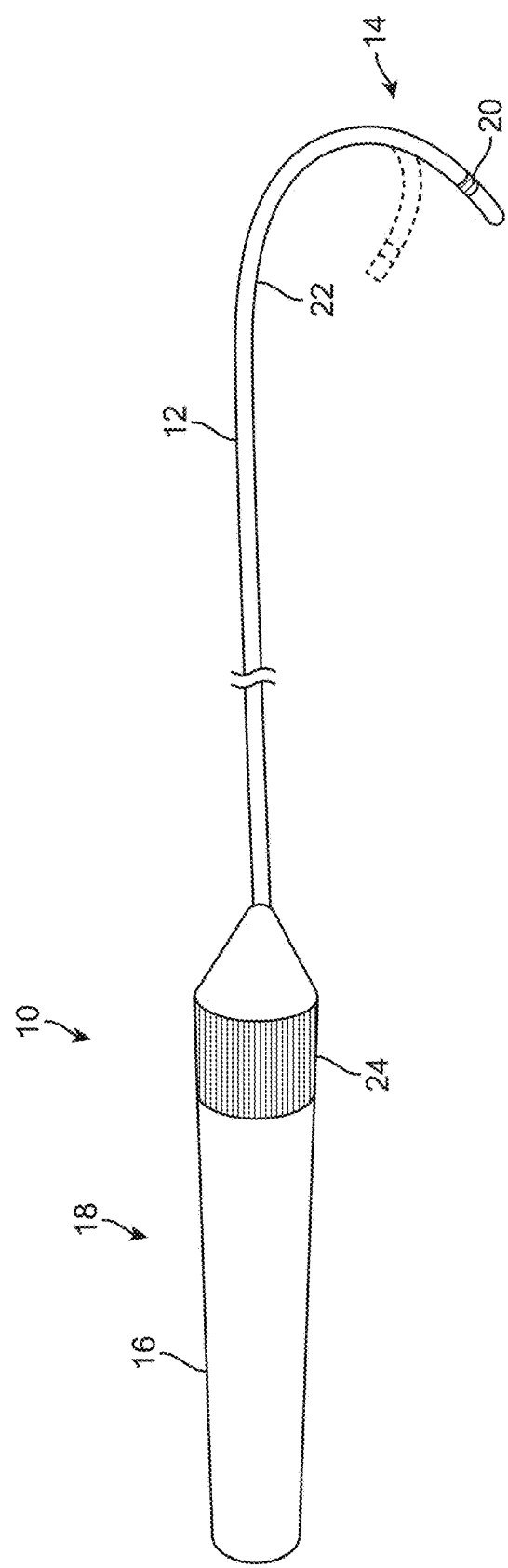
FIG. 1 illustrates an example catheter comprising an elongate shaft and a handle.
Figure 2:
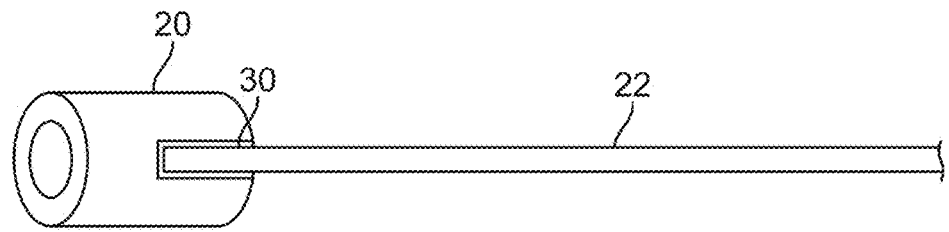
FIG. 2 illustrates a conventional pull ring having a slot which is laser cut into the wall of the tubing for insertion of the pull wire.
Figure 3:
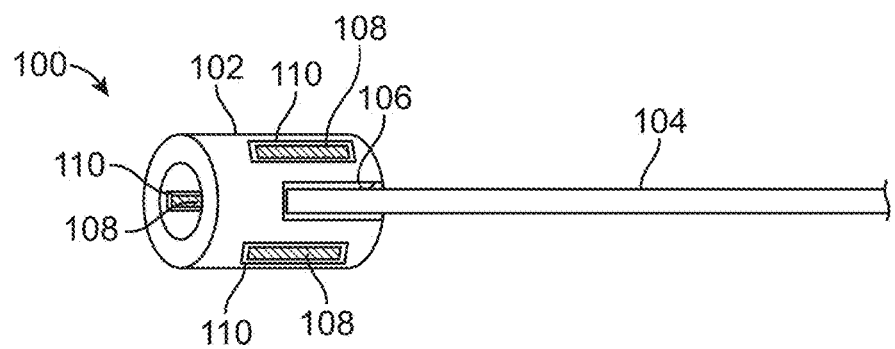
FIG. 3 illustrates an embodiment of an articulation device having at least one cut-out and at least one radiopaque insert.

FIG. 3 illustrates an embodiment of an articulation device 100 used to articulate a device or instrument, such as a catheter. In this embodiment, the articulation device 100 is comprised of a pull ring 102 having a tubular shape, sized and configured to extend around a distal end of an elongate shaft, such as a catheter shaft. In this embodiment, the articulation device 100 further comprises a pull wire 104 fixedly attached to the pull ring 102. It may be appreciated that the pull wire 104 has an elongate shape and may be comprised of a wire or ribbon. Typically, the pull ring 102 includes a notch 106 extending from one end of the pull ring 102 along a portion of its length so as to create sufficient surface area for bonding to the pull wire 104. The pull wire 104 is inserted into the notch 106 and fixed to the pull ring 102, such as by laser welding the pull wire 104 to the edges of the notch 106. This creates a secure bond able to provide high ultimate tensile strengths, such as 4-100 lbf. When the pull ring 102 is mounted on a shaft of a catheter or similar device, applying force to the pull wire 104 laterally bends the shaft in the direction of the pull wire 104 for articulation.

In this embodiment, the articulation device 100 further comprises at least one insert 108. Each insert 108 is insertable into a cut-out 110 of the pull ring 102. The cut-out 110 is a slot, window, groove or area where material has been removed from the wall of the tubular pull ring 102. Thus, the insert 108 is configured to be insertable into the cut-out 110 so that the insert is disposed within the wall of the pull ring 102 without increasing the thickness of the wall. The insert 108 is comprised of a material that is more visible or detectable under imaging techniques than the pull ring 102. For example, in some embodiments, the insert 108 is comprised of a radiopaque material that has a higher radiopacity than the pull ring 102. When the pull ring 102 is comprised of stainless steel, the insert 108 is comprised of a material having a higher radiopacity than stainless steel, such as platinum, gold, or any of their common alloys. In some embodiments, the insert 108 is comprised of a radiopaque wire, ribbon, sheet, or a polymer or ceramic material infused with, embedded with or compounded with radiopaque material. In particular, in some embodiments, the radiopaque insert 108 is comprised of platinum wire. In other embodiments, the radiopaque insert is comprised of a platinum marker band cut to a desired shape. The cut-out 110 may have any desired shape, such as rectangular, oval, round, circular, square, spiral, etc. Likewise, the cut-out 110 may have the shape of letters, words, numbers or symbols.

In any case, once the insert 108 is inserted into the cut-out 110, the insert 108 is fixed into place by any suitable method such as adhesive, soldering, swaging, welding, laser welding, etc. The insert 108 is flush with the walls of the pull ring 102 so as to not increase the outer diameter or decrease the inner diameter of the pull ring 102. This maintains the profile of the overall device, such as the French size of the catheter, which is highly desirable in fields where minimal French size is critical. Likewise, this maintains the inner diameter of the overall device, maximizing the area through which instruments and other devices can be passed through an internal lumen. This also does not add length to the pull ring 102, maximizing the flexibility of the catheter.

One or more radiopaque inserts 108 improves the radiopacity of the pull ring 102, allowing the pull ring 102 to be more visible and more easily identifiable under fluoroscopy than a conventional pull ring 102 without negatively altering other features such as tensile strength or overall dimensions of the pull ring 102. In addition, the radiopaque insert 108 is easily manufacturable. In some embodiments, the insert 108 is positioned in the cut-out 110 and fixed in place at the same time that the pull wire 104 is positioned in the notch 106 and fixed in place. This provides a simplified assembly process when assembling a catheter or instrument having the articulation device 100 wherein the articulation device 100 is attached to the catheter or instrument without the need for additional steps such as adding marker bands. In addition, with minimal inventory of insert material, such as wire, any size pull ring 102 can be enhanced for visualization. Such assembly techniques are less expensive than other techniques, such as gold plating, and allow more control over a desired visualization pattern, such as a higher concentration of radiopaque material in a particular area.

Figure 4:
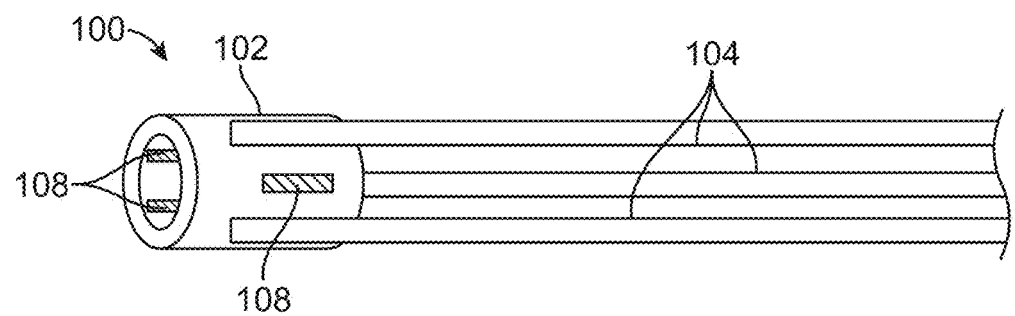
FIG. 4 illustrates an embodiment of an articulation device having three inserts and three pull wires, wherein each insert is disposed between a pull wire.

FIG. 3 illustrates an embodiment of an articulation device 100 having three radiopaque inserts 108, each insert 108 disposed in a rectangular cut-out 110 extending lengthwise along a portion of the length of the pull ring 102, parallel to the notch 106. In this embodiment, the inserts 108 are arranged around the circumference of the pull ring 102, such as equally spaced apart. It may be appreciated that a pull ring 102 may have more than one pull wire 104 so as to articulate the device in various directions. FIG. 4 illustrates an embodiment of an articulation device 100 having three inserts 108 and three pull wires 104, wherein each insert 108 is disposed between a pull wire 104.

Figure 5:
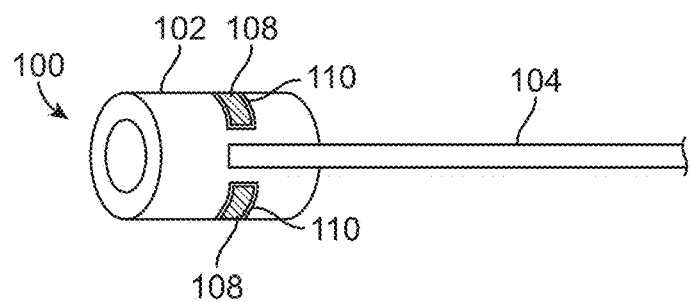
FIG. 5 illustrates an embodiment of an articulation device having an insert disposed within an arc shaped cut-out in the wall of the pull ring.

It may be appreciated that an articulation device 100 may include a variety of different types, shapes, and arrangements of inserts 108 and cut-outs 110. For example, FIG. 5 illustrates an embodiment of an articulation device 100 having an insert 108 disposed within an arc shaped cut-out 110 in the wall of the pull ring 102. In this embodiment, the cut-out 110 has a rectangular or strip shape extending perpendicularly away from the notch 106, at least partially around the circumference of the tubular pull ring 102 and ending on the other side of the notch 106. Thus, the insert 108 is visible under fluoroscopy for nearly 360 degrees of rotation of the pull ring 102 without interfering with the bond of the pull wire 104.

Figure 6:
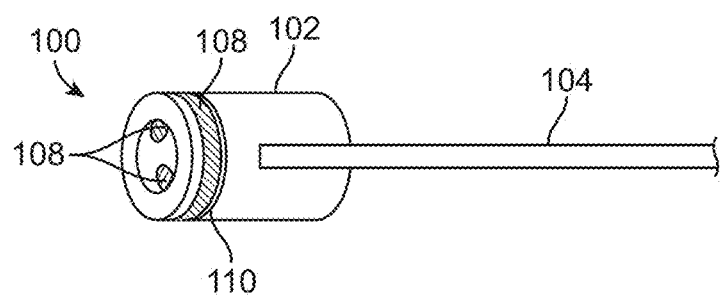
FIG. 6 illustrates another embodiment of an articulation device having an insert disposed within an arc shaped cut-out in the wall of the pull ring.

Similarly, FIG. 6 illustrates another embodiment of an articulation device 100 having an insert 108 disposed within an arc shaped cut-out 110 in the wall of the pull ring 102. In this embodiment, the cut-out 110 has a rectangular or strip shape extending around the circumference of the tubular pull ring 102 above the notch 106. However, the cut-out 110 is not continuous and a sufficient portion of the wall of the pull ring 102 remains between the ends of the cut-out 110 to maintain integrity and strength of the pull ring 102. Again, the insert 108 is visible under fluoroscopy for nearly 360 degrees of rotation of the pull ring 102 without interfering with the bond of the pull wire 104.

Figure 7:
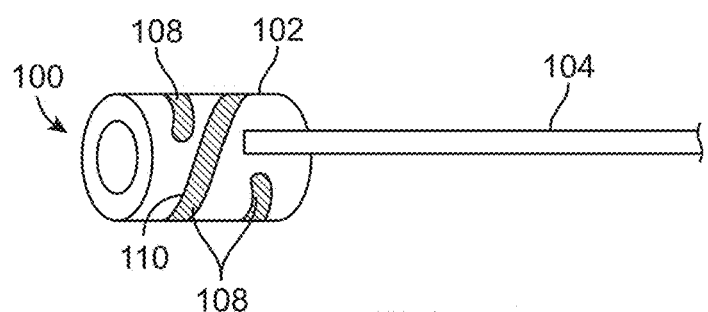
FIG. 7 illustrates an embodiment of an articulation device having an insert disposed within a spiral shaped cut-out in the wall of the pull ring.

FIG. 7 illustrates another embodiment of an articulation device 100 having an insert 108 disposed within an arc shaped cut-out 110 in the wall of the pull ring 102. In this embodiment, the cut-out 110 has a spiral shape wherein the cut-out 110 extends completely around the circumference of the tubular pull ring 102 in a spiral configuration. Again, a sufficient portion of the wall of the pull ring 102 remains to maintain integrity and strength of the pull ring 102. And, the insert 108 is visible under fluoroscopy or other imaging techniques for 360 degrees of rotation of the pull ring 102 without interfering with the bond of the pull wire 104.

Figure 8:
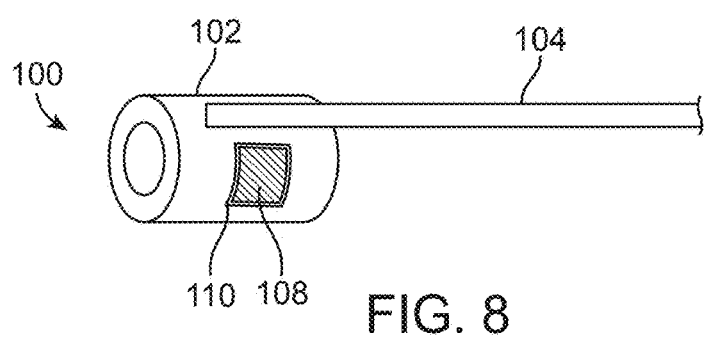
FIG. 8 illustrates an embodiment of an articulation device having an insert disposed within a geometrically shaped cut-out in the wall of the pull ring.
Figure 9:
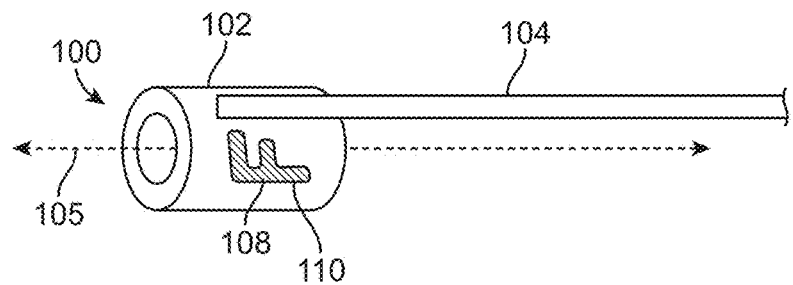
FIG. 9 illustrates an embodiment wherein the cut-out has the shape of a letter.

FIG. 8 illustrates an embodiment of an articulation device 100 having insert 108 disposed within a geometrically shaped cut-out 110 in the wall of the pull ring 102. In this embodiment, the cut-out 110 has a square shape. Thus, the corresponding insert 108 has a square shape and may be comprised of a sheet or other flat material cut to fit the square shape. For example, the insert 108 may be cut from a conventional marker band and fixed within the cut-out 110. In this embodiment, the square shaped cut-out 110 is disposed on one side of the pull ring 102. Therefore, visualization of the square shaped cut-out under fluoroscopy or other imaging techniques indicates the rotational orientation of the pull ring 102 in addition to the transitional location of the pull ring 102 within the anatomy. It may be appreciated that the cut-out 110 may have other geometric shapes, such as triangular, round, oval, etc. It may also be appreciated that the cut-out 110 may have the shape of a letter, word, number or symbol. For example, FIG. 9 illustrates an embodiment wherein the cut-out 110 has the shape of the letter F. Some shapes, such as the letter F, can indicate rotational orientation of the pull ring 102 along its longitudinal axis 105 while also indicating translational and rotational orientation within a plane of the anatomy. For example, when the embodiment of FIG. 9 is visualized wherein the letter F is in an upside-down arrangement, it is known that the pull ring 102 (and therefore distal end of the catheter) is pointed downward in an x-y plane of the anatomy. Likewise, the amount of the letter F that is visible indicates the rotational orientation of the pull ring 102 around its own longitudinal axis 105. It may also be appreciated that the cut-out 110 may have the shape of a word or logo.

It may be appreciated that a pull ring 102 may have a variety of different shaped cut-outs 110 and inserts 108. For example, in some embodiments the pull ring 102 has cut-outs of various shapes extending around the circumference of the pull ring 102, such as a square, circle and triangle. Thus, the shapes provide indication of rotational orientation of the pull ring 102 around its own longitudinal axis 105 under visualization.

In some embodiments, the type of insert 108 indicates rotational orientation of the pull ring 102 under fluoroscopic imaging. For example, in some embodiments the pull ring 102 includes a plurality of cut-outs 110 wherein each cut-out 110 has an insert 108 of differing material or differing radiopacity. Thus, inserts 108 having increasing radiopacity may be disposed circumferentially around the pull ring 102. Thus, the rotational orientation of the pull ring 102 around its longitudinal axis 105 may be determined under fluoroscopy based on the degree of radiopacity of the insert 108 that is visible.

Figure 10:
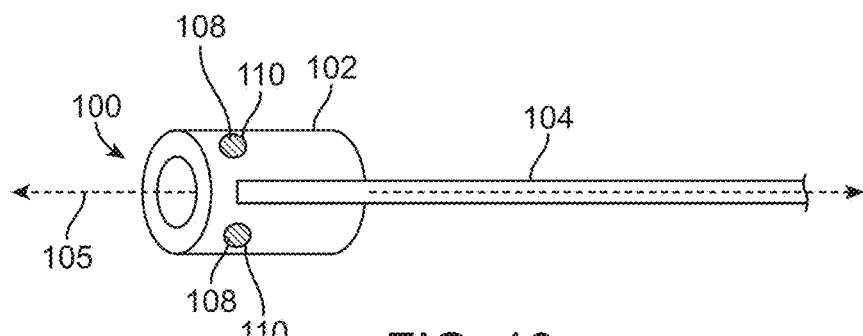
FIG. 10 illustrates an embodiment of a pull ring having circular cut-outs disposed around its circumference wherein the cut-outs are filled with inserts comprising a polymer or ceramic containing a radiopaque material.

FIG. 10 illustrates an embodiment of a pull ring 102 having circular cut-outs 110 disposed around its circumference. In this embodiment, the cut-outs 110 are filled with inserts 108 comprising a polymer or ceramic containing a radiopaque material. In some embodiments, the quantity of radiopaque material varies so as to create inserts 108 of varying radiopacities. As mentioned above, inserts 108 having increasing radiopacity may be disposed circumferentially around the pull ring 102. Thus, the rotational orientation of the pull ring 102 may be determined under fluoroscopy based on the degree of radiopacity of the insert 108 that is visible.

Figure 11A:
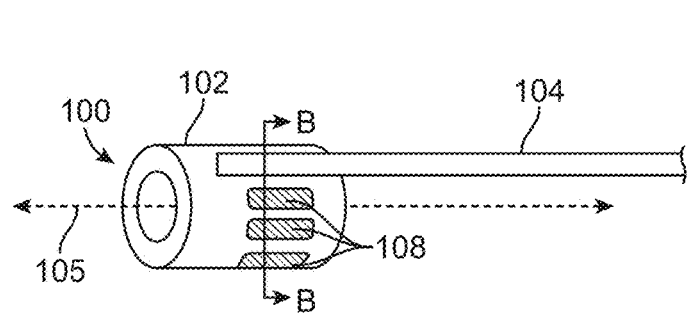
FIGS. 11A-11B illustrate an embodiment wherein the pull ring includes a plurality of inserts disposed adjacent to each other along the circumference of the pull ring.
Figure 11B:
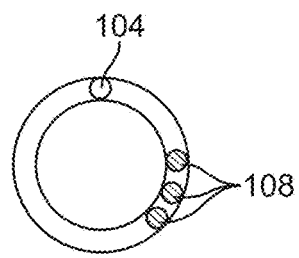

FIGS. 11A-11B illustrate an embodiment wherein the pull ring 102 includes a plurality of inserts 108 disposed adjacent to each other along the circumference of the pull ring 102. In this embodiment, three inserts 108 are present. FIG. 11B illustrates a cross-section of the pull ring 102 of FIG. 11A across segment B-B. Thus, three inserts 108 are shown disposed within the wall of the tubular pull ring 102. In such embodiments, rotational orientation of the pull ring 102 around its longitudinal axis 105 under fluoroscopic imaging is indicated by the number of inserts 108 that are visible.

Figure 12:
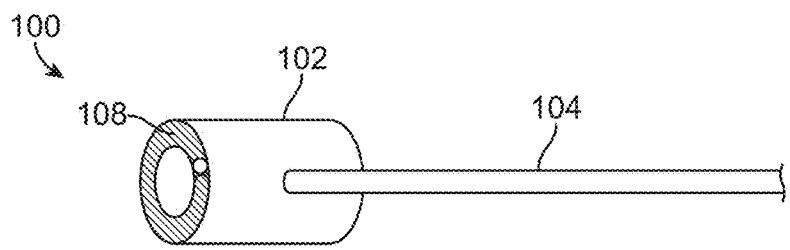
FIG. 12 illustrates an embodiment wherein the insert is fixedly attached to an end of the pull ring so that the insert covers the circular cross-sectional edge of the tubular walls of the pull ring.
Figure 13:
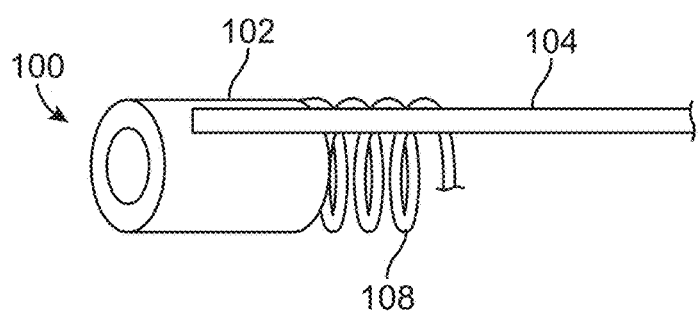
FIG. 13 illustrates an insert having the shape of a spring wherein one end of the spring-shaped insert is fixedly attached to the pull ring while the other end remains free.

In some embodiments, the insert 108 is disposed along an end of the pull ring 102. For example, FIG. 12 illustrates an embodiment wherein the insert 108 is fixedly attached to an end of the pull ring 108 so that the insert 108 covers the circular cross-sectional edge of the tubular walls of the pull ring 108. When the insert 108 comprises a wire, the wire forms a ring which is fixedly attached to the end of the pull ring 108. It may be appreciated that in some embodiments, the insert 108 extends around a portion of the end surface of the pull ring 108, such as in an arc shape. Likewise, more than one insert 108 may be fixed to the end surface of the pull ring 108, such as leaving gaps between them. Further, one or more inserts 108 may be fixedly attached in a stacked configuration. Still further, the insert 108 may have the shape of a spring wherein one end of the spring-shaped insert 108 is fixedly attached to the pull ring 108 while the other end remains free, as illustrated in FIG. 13.

It may be appreciated that any number and combination of types of cut-outs 110 may be formed in a pull-ring 102. Likewise, any number and combination of types of inserts 108 may be applied to a pull-ring 102. Further, a pull ring 102 may include both at least one cut-out 110 having an insert 108 and at least one insert 108 fixedly attached to an end surface of the pull ring 102. In some embodiments, the pull ring 102 having at least one insert 108 is utilized without a pull wire 104, to aid in visualization.

It may be appreciated that the pull rings 102 may have any suitable size or shape for a given application. Pull rings 102 typically have inner diameters that range in size from 0.014 inches to 0.500 inches and wall thicknesses that typically range in size from 0.0015 inches to 0.020 inches. It may be appreciated that larger pull rings 102 typically require larger wall thicknesses to maintain structural integrity. Pull wires 104 are typically wires or ribbons having a thickness of 0.002 inches to 0.020 inches. When ribbons are used, the thickness may be as low as 0.001 inches. In any case, the pull wires 104 are typically welded to the outside of the pull ring 102, inside of the pull ring 102 or into a notch 106 cut into the end of the pull ring 102. Thus, conventional or specialty pull rings 102 and pull wires 104 may be utilized wherein the pull rings 102 are modified to incorporate inserts 108 according to the present invention. Such modifications provide improved visualization of remotely articulating portions of devices or instruments without compromising design features such as profile, inner diameter, outer diameter, flexibility or strength.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An articulation device comprising:
   a tubular pull ring having a first end, a second end and a circumferential wall, wherein the circumferential wall includes at least one cut-out;
   at least one radiopaque insert fixedly inserted into the at least one cut-out so that the at least one radiopaque insert is disposed within the circumferential wall without increasing a thickness of the circumferential wall; and
   a pull wire fixedly attached to the tubular pull ring,
   wherein the tubular pull ring is mountable on a distal end of a shaft so that application of force to the pull wire articulates the distal end of the shaft.

2. The articulation device of claim 1, wherein the radiopaque insert comprises a wire.

3. The articulation device of claim 1, wherein the radiopaque insert comprises a ribbon or a sheet.

4. The articulation device of claim 1, wherein the radiopaque insert comprises a polymer embedded with radiopaque material or a ceramic embedded with radiopaque material.

5. The articulation device of claim 1, wherein the radiopaque insert has a higher radiopacity than the tubular pull ring.

6. The articulation device of claim 5, wherein the radiopaque insert is comprised of platinum or gold.

7. The articulation device of claim 5, wherein the tubular pull ring is comprised of stainless steel.

8. The articulation device of claim 1, wherein the at least one cut-out has a rectangular, oval, round, circular, square or spiral shape.

9. The articulation device of claim 1, wherein the at least one cut-out has a shape of a letter, word, number, symbol or logo.

10. The articulation device of claim 1, wherein the radiopaque insert is fixedly inserted by adhesive, soldering, swaging, welding, or laser welding the radiopaque insert to the tubular pull ring.

11. The articulation device of claim 1, wherein the at least one cut-out is disposed along the wall of the tubular pull ring in an arrangement which provides an indication of rotational orientation of the tubular pull ring around its longitudinal axis when visualized from one side.

12. The articulation device of claim 1, further comprising at least one additional pull wire fixedly attached to the tubular pull ring, wherein the at least one cut-out is disposed between fixation points of the pull wire and the at least one additional pull wire to the tubular pull ring.

13. An articulation device comprising:
    a tubular pull ring having a first end, a second end and a circumferential wall,
    at least one radiopaque wire or ribbon fixedly attached to an end surface of the first end or second end of the tubular pull ring without increasing a thickness of the circumferential wall; and
    a pull wire fixedly attached to the tubular pull ring,
    wherein the tubular pull ring is mountable on a distal end of a shaft so that application of force to the pull wire articulates the distal end of the shaft.

14. The articulation device of claim 13, wherein the at least one radiopaque wire or ribbon has the shape of a ring.

15. The articulation device of claim 13, wherein the at least one radiopaque wire or ribbon has the shape of a coil.

* * * * *

UNITED STATES PATENT AND TRADEMARK OFFICE
CERTIFICATE OF CORRECTION

PATENT NO. : 10,279,147 B2
APPLICATION NO. : 15/612575
DATED : May 7, 2019
INVENTOR(S) : Marcos T. Contreras and Ronald G. Williams Page 1 of 1

It is certified that error appears in the above-identified patent and that said Letters Patent is hereby corrected as shown below:

On the Title Page

The title (54), should read -- ARTICULATION DEVICES HAVING INCREASED VISIBILITY --

Signed and Sealed this
Fifth Day of November, 2019

Andrei Iancu
*Director of the United States Patent and Trademark Office*